(12) United States Patent
Raymondos

(10) Patent No.: US 9,867,956 B2
(45) Date of Patent: Jan. 16, 2018

(54) MEDICAL DEVICE FOR CONDUCTING A MEDICAL EXAMINATION AND/OR INTERVENTION WITHIN A HUMAN OR ANIMAL BODY

(75) Inventor: Konstantinos Raymondos, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 397 days.

(21) Appl. No.: 14/125,724

(22) PCT Filed: Jun. 15, 2012

(86) PCT No.: PCT/EP2012/061499
§ 371 (c)(1),
(2), (4) Date: Mar. 14, 2014

(87) PCT Pub. No.: WO2012/172076
PCT Pub. Date: Dec. 20, 2012

(65) Prior Publication Data
US 2014/0194684 A1 Jul. 10, 2014

(30) Foreign Application Priority Data
Jun. 15, 2011 (EP) .................................... 11004866

(51) Int. Cl.
*A61B 1/267* (2006.01)
*A61M 16/04* (2006.01)
(Continued)

(52) U.S. Cl.
CPC ....... *A61M 16/0488* (2013.01); *A61B 1/0008* (2013.01); *A61B 1/00181* (2013.01);
(Continued)

(58) Field of Classification Search
CPC ......... A61B 1/267; A61B 1/05; A61B 1/2676; A61M 16/0488; A61M 16/04
(Continued)

(56) References Cited

U.S. PATENT DOCUMENTS 6,718,970 B2 * 4/2004 Sniadach .......... A61M 16/0488
128/200.26
8,529,442 B2 * 9/2013 Pacey ................ A61B 1/00142
600/187
(Continued)

FOREIGN PATENT DOCUMENTS

EP 1 307 131 B2 11/2010

*Primary Examiner* — Alexandra L Newton
(74) *Attorney, Agent, or Firm* — Whitham, Curtis & Cook, P.C.

(57) ABSTRACT

The invention is related to a medical device (1) for conducting a medical examination and/or intervention within a human or animal body, the medical device (1) comprising a handle (2) and a curved guiding bar (3) connected to the handle (2), the guiding bar (3) comprising a guiding duct (4) adapted for guiding a medical instrument (5) from the handle area to a distal end (7) of the guiding bar (3) which is distant from the handle (2), the guiding bar (3) comprising on its distal end (7) a first camera (6) which is integrated within the guiding bar (3) or attached to the guiding bar (3), whereby the first camera (6) is arranged and adjusted for capturing an area (8) in front of the distal end (7) of the guiding bar (3).

24 Claims, 5 Drawing Sheets

(51) Int. Cl.
 *A61B 1/00* (2006.01)
 *A61B 1/018* (2006.01)
 *A61B 1/05* (2006.01)
(52) U.S. Cl.
 CPC .......... *A61B 1/00183* (2013.01); *A61B 1/018* (2013.01); *A61B 1/05* (2013.01); *A61B 1/267* (2013.01); *A61B 1/2673* (2013.01)
(58) Field of Classification Search
 USPC .................................................. 600/120, 188
 See application file for complete search history.

(56) References Cited

U.S. PATENT DOCUMENTS

| | | |
|---|---|---|
| 2006/0020171 A1 | 1/2006 | Gilreath |
| 2006/0065268 A1 | 3/2006 | Koyama et al. |
| 2006/0162730 A1 | 7/2006 | Glassenberg |
| 2006/0180155 A1* | 8/2006 | Glassenberg .......... A61B 1/267 |
| | | 128/207.15 |
| 2009/0299139 A1 | 12/2009 | Yamakawa |
| 2011/0137127 A1 | 6/2011 | Schwartz |

\* cited by examiner

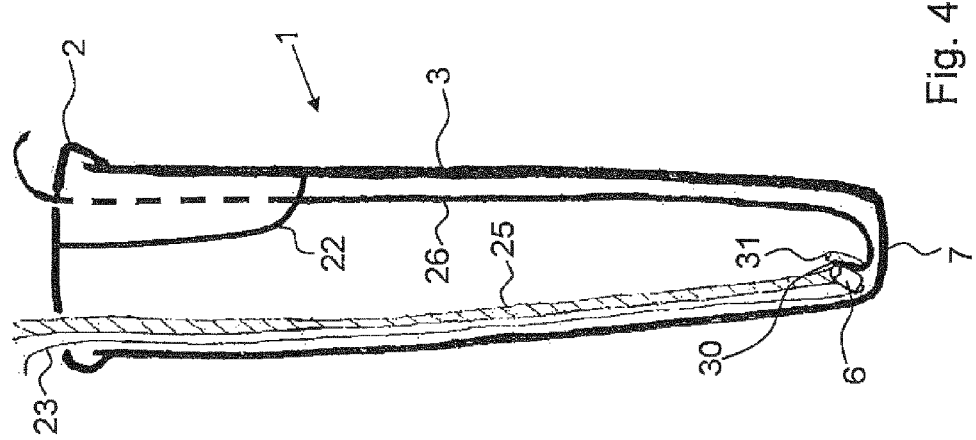
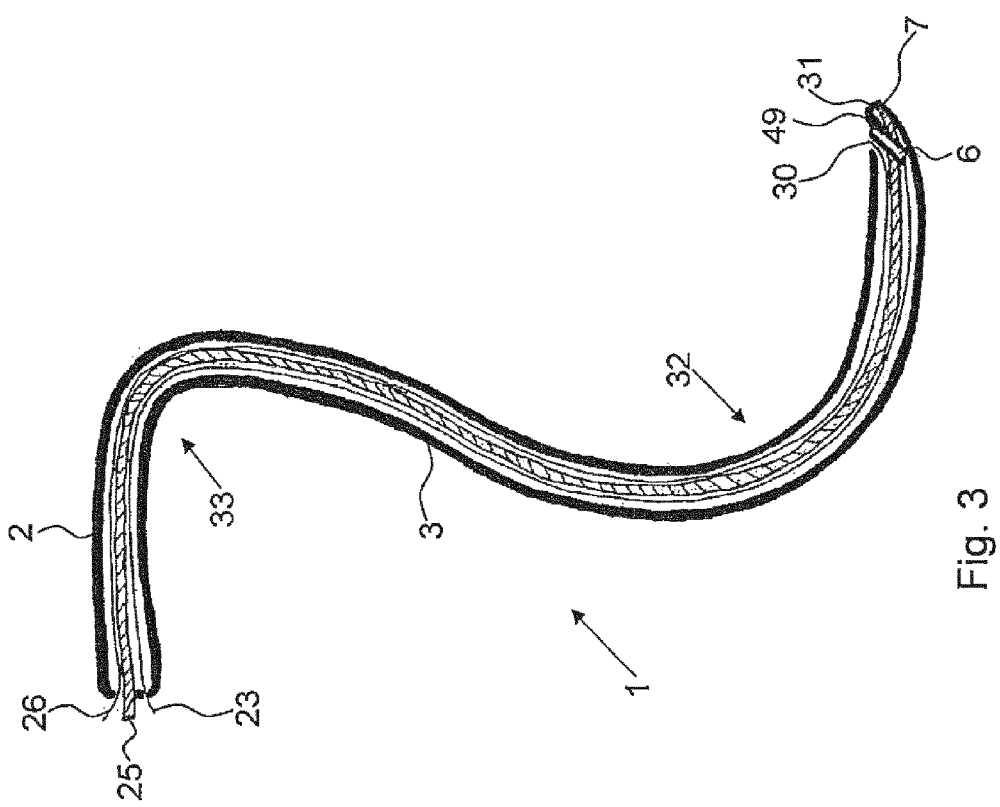

MEDICAL DEVICE FOR CONDUCTING A MEDICAL EXAMINATION AND/OR INTERVENTION WITHIN A HUMAN OR ANIMAL BODY

FIELD OF THE INVENTION

The invention is related to a medical device for conducting a medical examination and/or intervention within a human or animal body according to claim 1. The device can be used e.g. for conducting a laryngoscopy, an intubation and/or for medical interventions in the area of otolaryngology.

BACKGROUND

In the area of laryngoscopy and endotracheal intubation several difficulties can occur, in particular in case of challenging airways, like airways with anatomical anomalies, e.g. airways which are small in diameter and/or comprise curved portions which require high bending angles for an oral-tracheal tube, or airways with pathological changes like tumors. Even in cases with normal airways problems can occur, in particular in emergency situations or due to lack of experience.

A laryngoscopy is a medical method of examination of the larynx. An intubation is an insertion of a tube, in particular an oral-tracheal tube, through an oral airway into the trachea. An intubation normally requires a device for laryngoscopy, for example the so-called laryngoscope. Such a laryngoscope normally includes guiding elements for guiding the tube.

A known medical device is disclosed in EP 1 307 131 B2. In practical use this device is difficult to operate. In particular, it is difficult to enter an oral-tracheal tube into the trachea with the known device, especially in case of challenging airways like small mouth openings, anatomical anomalies or pathological changes.

SUMMARY

It is an object of the present invention to provide a medical device which allows for conducting a medical examination and/or intervention within a human or animal body in an easier and safer manner, both for normal and for challenging airways.

This object is achieved by a medical device for conducting a medical examination and/or intervention within a human or animal body, the medical device comprising a handle and a curved guiding bar connected to the handle, the guiding bar comprising a guiding duct adapted for guiding a medical instrument from the handle area to a distal end of the guiding bar which is distant from the handle, the guiding bar comprising on its distal end a first camera which is integrated within the guiding bar or attached to the guiding bar, whereby the first camera is arranged and adjusted for capturing an area in front of the distal end of the guiding bar.

The medical instrument can be any kind of medical tool like a tube, e.g. an oral-tracheal tube, a laser or other tools usually used in the area of otolaryngology.

The medical device can be designed for conducting a medical examination and/or intervention within a human or animal body without lifting the epiglottis or the tongue base. In such case, the medical device can be constructed without a lifter for lifting the epiglottis or the tongue base.

Compared with known devices, the medical device can be designed more compact since there is no need for providing bulky elements in the front area like a lifter. The medical device is therefore much easier to us in practical situations. The operator of the device has substantially more freedom for guiding the device through the upper airways and for placing it in the correct position for introducing the medical instrument into the trachea. In contrast, medical devices having a lifter or spatula at the distal end considerably limit the possibilities for changing the position of the medical device when introduced in the oral airways of a patient. A further advantage is that, since no element extending from the front of the distal end of the guiding bar is required, the capturing area of the first camera is not disturbed or masked by such elements. Instead, there is a free view on the vocal cords possible, which is not disturbed, for example, by the epiglottis or the tongue base. The medical device allows for an improved viewing angle which permits a free, undisturbed view on the vocal cords.

Another very important advantage is that with the medical device of the invention a laryngoscopy and/or an intubation can be done easily in an awake state of a patient without general but only local anaesthesia. This increases the safety of endotracheal intubation enormously as intubation can be performed with sustained reflexes like coughing and swallowing during spontaneous breathing. General anaesthesia before endotracheal intubation enables to tolerate the current quite invasive standard of laryngoscopy and intubation. However, when intubation fails asphyxia may occur. In contrast to all current methods of conventional laryngoscopy and videolaryngoscopy the medical device of the invention facilitates laryngoscopy and/or intubation in awake patients due to its very compact and extremely flat design of the guiding bar. This avoids unnecessary irritations of the patient because lifting of the tongue base and the epiglottis is not necessary. This would not be possible with all current medical devices having a lifter or spatula at the distal end. The pressure on the tongue base results in suffocating or vomiting that cannot be abolished by superficial, local anaesthesia.

The medical device, in particular the guiding bar, can be designed very compact which makes it possible to conduct intubation also with persons with an mouth opening less than 1.5 cm.

It is a further advantage of the medical device that it makes a laryngoscopy and/or an intubation possible without lifting the epiglottis or the tongue base. This means that no active lifting of the epiglottis or tongue base is required during use of the medical device. A slight contact between the guiding duct of the medical device and the tongue base or the epiglottis is still possible and is not disadvantageous. However, an explicit and considerable lifting of the epiglottis or tongue base is not necessary.

The medical device can also be used in the area of otolaryngology, for example for guiding curve-shaped medical instruments, including a laser device.

The medical device advantageously comprises a first camera on the distal end of the guiding bar. The camera can be installed in an area around the distal end but very close to the distal end. It is advantageous to install the camera not more than 15 mm away from the distal end. This supports an advantageous capturing angle and allows a free view on the vocal cords. In particular, the first camera shall not be placed above the position where the medical instrument exits the guiding duct.

The optimum placement of the first camera in the guiding bar allows for an optimum view on the vocal cords in a perspective from below the entry of the trachea, whereby the vocal cords appear approximately in the centre of the pictures delivered by the first camera. Compared to other medical devices using optical image gathering devices, the free view of the camera is not disturbed by structures of the larynx, like the arytenoid cartilage or the epiglottis.

Another advantage is that the camera can be guided very close to the entry of the trachea so that there is a direct view into the trachea to the vocal cords. In addition, such short design of the guiding bar allows for an improved outlet angle of the medical instrument so that the medical instrument can be guided easily into the trachea. False intubations into the esophagus can be avoided.

The handle and the guiding bar can be made of piece of material or of different pieces connected together.

The medical instrument can be inserted through the guiding bar without any lubricant, but however a lubricant can be used in addition. After insertion of the medical instrument into the trachea the medical device can easily be removed from the patient without the risk to extract the medical instrument.

Specific patients have the risk that the contents from the stomach get back through the esophagus to the larynx region which could result in a blocking of suction channels through debris from the stomach. In such cases a special tube can be used instead of the normal oral-tracheal tube. The special tube comprises a powerful chirurgical suction device. The tip of the special tube is cone-shaped and comprises, compared to conventional oral-tracheal tubes, a thin outer wall with a large inner diameter of up to 10 mm. The special tube comprises a cuff balloon which can be filled with air to seal the trachea. Below the cuff balloon are several side openings in the wall which serve to increase the suction performance and to ensure a sufficient suction efficiency also in cases if the large main suction opening adheres or becomes blocked. The special tube can be introduced with a medical device in the same way as the oral-tracheal tube. In particular, the special tube can be guided under optical control in the same manner as described before to the location where suction shall be performed. The special tube is to be connected to a powerful external suction pump.

According to an advantageous embodiment of the invention, an angle between a central line of the area captured by the first camera and insertion direction of the medical instrument into the guiding duct is smaller than an angle between a hypothetical straight extension line of the guiding bar from its distal end and the insertion direction of the medical instrument. This allows for a capturing direction of the camera and a view perspective which is to a certain extent steeper than the direction of the distal end of the guiding bar. This provides for a kind of viewing perspective from below up to the entry of the trachea, resulting in an optimum view on the vocal cords. This has the further advantage that the view cannot be disturbed by the epiglottis, since it is possible to guide the distal end of the guiding bar together with the first camera under the epiglottis directly in front of the vocal cords.

According to an advantageous embodiment of the invention the guiding bar or other elements of the medical device which are inflexibly connected to the guiding bar do not extend from the distal end of the guiding bar into the capturing area of the first camera. This has the advantage that the guiding bar and the mentioned other elements cannot disturb or cover the free view of the first camera within the whole capturing area.

According to an advantageous embodiment of the invention the guiding duct extends over the whole length of the guiding bar and is arranged for providing a supporting face for the medical instrument within the guiding duct so that the medical instrument lies against the guiding duct. This has the advantage that no further elements are necessary for guiding and supporting the medical instrument. In particular, no elements which could potentially increase an undesired friction of the medical instrument are required. The supporting face for the medical instrument can extend over the whole length of the guiding duct or at least partially along the guiding duct. It is particularly advantageous if the medical instrument is supported by the supporting face in the medium and distal area of the guiding bar, in order to allow precise guiding of the medical instrument in the area where the medical instrument exits from the guiding bar. This supports the compact design of the guiding bar with very small dimensions which leads to an improved practical handling of the medical device.

According to an advantageous embodiment of the invention the guiding bar comprises a second camera which is integrated within the guiding bar or attached to the guiding bar between the handle and the distal end but being closer to the handle than the first camera, the second camera is arranged and adjusted for capturing the distal end of the guiding bar and a surrounding area. This has the advantage that the operator of the medical device can be provided with a second viewing area on a screen showing the pictures of the second camera. Since the second camera captures the distal end of the guiding bar and a surrounding area, the operator gets helpful information about the actual position of the distal end of the guiding bar in relation to the surrounding area which helps the operator to lead the guiding bar to the entry of the trachea. With the view perspective of the second camera it is possible for the operator to identify the epiglottis or other obstacles within the desired guiding path during introduction of the guiding bar into a patient.

The first camera and/or the second camera can be of a CCD camera type. The first and/or the second camera can comprise an illumination device for illuminating the capturing area of the camera. The illumination device can also be installed separately from the first and/or second camera. According to an advantageous embodiment of the invention, an illumination device is integrated within the guiding bar or attached to the guiding bar, for example in the distal end area.

The first and/or second camera can be built together with the illumination device. It is today possible to manufacture such a unit with a cross-section of only 4 mm. As an alternative, a light guide can be used, for example a polymer light guide.

According to an advantageous embodiment of the invention the handle shows away from the thorax of a patient if the medical device is introduced into the patient in the course of conducting a laryngoscopy and/or an intubation. For example, the handle can show away in a vertical direction from the thorax of a horizontally lying patient, or in a horizontal direction towards the head of the patient, or in any direction in between or close to the aforementioned directions. This has the advantage that the medical device can be better operated, in particular, in cases of adipose patients. In such cases, the handle showing away from the thorax of the patient can be operated without limitations of space due to the advantageous direction of the handle. According to an advantageous embodiment of the invention the handle shows in the direction of the head of the patient. This has the further advantage that the way of holding the medical device is different to conventional standard tools of laryngoscopy, like the Macintosh laryngoscope. With the Macintosh laryngoscope the user has to lift the handle upwards with considerable force. This is avoided by the different handle position of the invention that enables the operator to use a very different kind of motion sequence that is more precise and effective.

According to an advantageous embodiment of the invention, a longitudinal axis of the handle is approximately perpendicular to a plane which is spanned by the first bending area of the medical device. This has the advantage that the handle shows away both from the thorax and the head of the patient, because the handle is pointing to the left or right side of the patient if the medical device is introduced into the patient's larynx. According to an advantageous embodiment of the invention, the medical device comprises a handle with two sections, with the guiding bar being fixed to the medical device between the two sections. For example, a first section of the handle could point to the left side of the patient and a second portion of the handle could point to the right side of the patient during use of the medical device in conducting a laryngoscopy. In this way, the two portions of the handle can be designed similar to a handle bar of a bicycle or motorcycle. In a further advantageous embodiment of the invention, the first portion of the handle can comprise control elements for controlling a flushing mechanism of the medical device, and the second portion can comprise control elements for controlling a suction mechanism of the medical device.

According to an advantageous embodiment of the invention, the guiding bar is connected to the handle via an articulated joint which allows positioning of the handle in different angles relative to the guiding bar. The articulated joint can be designed e.g. like a hinge. This has the advantage that the handle can be positioned in different angles relative to the guiding bar so that a user can choose an appropriate angle which allows convenient use of the medical device. In case of a handle having a first section and a second section, as mentioned before, each section of the handle can be connected through an articulated joint to the guiding bar. According to an advantageous embodiment of the invention, the articulated joint comprises a notch mechanism which allows an easy fixation of the angular position of the handle relative to the guiding bar through a number of predefined notching positions. In other embodiments, the handle can be fixed in a desired angular position relative to the guiding bar through a fixation screw or a clamping mechanism.

According to an advantageous embodiment of the invention the guiding bar comprises a first bending area of at least 90°. The first bending area can be a curved bending area in an end area of the guiding bar distant from the handle. This allows for an optimum adaptation of the shape of the guiding bar to the form and shape of human airways. As a result, the medical device can be easily inserted and ducted to the entry of the trachea, which in particular eases operation in case of challenging airways.

Another advantage is that the medical device, once it is placed in its final position within the patient's airways, it is automatically held in position due to its optimum adaptation to the shape of the airways. Only very limited corrective movements might in specific cases be required.

According to an advantageous embodiment of the invention the first bending area comprises the same bending radius over an arc angle of at least 80°. Such design of the guiding bar creates an optimum adaptation to the human airways. Another advantage is that the friction-related resistance when inserting the medical instrument through the guiding duct remains relatively constant or increases only slightly, but not in steps or progressive.

According to an advantageous embodiment of the invention, the guiding bar is on the inside of the first bending area at least partially open. This allows for a compact design of the guiding bar with a very low height of the guiding bar, since no top closing element of the guiding bar is required. This further improves the ability of the medical device to be used successfully with patients with challenging airways. Further, the weight of the medical device can be reduced. The inside of the first bending area can be partially open or completely open. For example, there could be open and closed sections.

Through its partially open design on one side the medical device can be easily removed once the medical instrument is placed in its final position. The medical device can be removed from the patient in one part form, which means without any need for dismounting of parts of the medical device or any risk of extracting the medical instrument, as it is required by other devices.

According to an advantageous embodiment of the invention the guiding bar comprises a second bending area of at least 90° in the junction area of the guiding bar and the handle. This allows for an ergonomic design of the medical device. An operator can easily and ergonomically use the medical device in all situations of laryngoscopy and/or intubation. In an advantageous embodiment of the invention the second bending area has a bending direction opposite to the bending direction of the first bending area. This further improves the ergonomics of the medical device. In an advantageous embodiment of the invention, the assembly comprising the handle and the guiding bar has an S-shape when viewed from the side.

A further optimisation is achieved by including an integrated flushing and suction system which serves to improve the visibility in all situations, also in case of conglomeration of blood, secretion or content from the stomach.

According to an advantageous embodiment of the invention, the medical device comprises a flushing channel or a flushing duct for insertion of a flushing conduct, the flushing channel or the flushing duct being integrated within the guiding bar or attached to the guiding bar. The flushing channel or the flushing conduct has at least one emission opening for emitting a flushing medium, wherein the at least one emission opening is located at the distal end of the guiding bar. The at least one emission opening is adjusted in a way that emitted flushing medium is directed to the first and/or second camera. By use of the flushing medium, e.g. a liquid like water, the first and/or second camera can be cleaned. This allows for maintaining a clear optical vision of the first and/or second camera during conductance of a laryngoscopy and/or an intubation.

According to an advantageous embodiment of the invention, the medical device comprises a first suction channel or a first suction duct for inserting a first suction conduct, the first suction channel or the first suction duct being integrated within the guiding bar or attached to the guiding bar. The first suction channel or the first suction conduct comprises a first suction opening which is located at the distal end of the guiding bar. The first suction channel or the first suction conduct allows for removing liquids and other debris in the area of the distal end of the guiding bar.

According to an advantageous embodiment of the invention the medical device comprises a second suction channel or a second suction duct for inserting a second suction conduct, the second suction channel or the second suction duct being integrated within the guiding bar or attached to the guiding bar. The second suction channel or the second suction conduct comprises a second suction opening which is located at the distal end of the guiding bar, wherein the second suction opening is adjusted in a way that flushing medium is extractable by suction. Advantageously the second suction opening can be located on the opposite side of the first camera in relation to the emission opening for emitting the flushing medium. This allows for easy and nearly complete removal of the flushing medium.

The flushing conduct, the first and the second suction conduct can be provided in the form of flexible tubes or catheters. Compared to the oral-tracheal tube, the conduct tubes shall be significantly smaller in diameter.

The flushing channel advantageously has a diameter of about one millimeter.

The flushing channel as well as the first suction channel and the second suction channel can be connected through tubes via a Luer-Lock connector to a standard infusion system. Such a combined suction/flushing-drainage system allows for a permanent gathering of images with high quality without disturbance through liquids and/or debris within the larynx. This allows for suction of liquids and debris in front of the elongate body which reduces the risk of an entry of gastric juice into the trachea.

According to an advantageous embodiment of the invention one or more of the following elements are included within the handle:
a) a liquid container in the form of a reservoir for flushing medium,
b) a pumping mechanism for delivery of flushing medium, the pumping mechanism being connected to the reservoir for flushing medium,
c) a liquid container in the form of a storage for liquids gathered through a suction channel or a suction conduct through suction,
d) a suction mechanism for removal of liquids, which is connected to the liquid container.

This allows for a high degree of integration of the aforementioned useful elements of the medical device. Further, the need for connection of external tubes for the flushing medium or media extracted by suction can be minimised or removed. This allows for an improved freedom of using and operating the medical device. The pumping mechanism for delivery of flushing medium and/or the suction mechanism for removal of fluids can be of a mechanical bellow type or a piston type, e.g. like the mechanism in a spray gun.

According to an advantageous embodiment of the invention, a picture processing unit is coupled to the first and/or second camera, the picture processing unit being arranged for processing of the pictures delivered by the first and/or second camera by means of pattern recognition and for identifying the actual position of the distal end of the medical device during a laryngoscopy and/or intubation within the patient, whereby the picture processing unit is arranged for generating route guidance data based on the identified actual position of the distal end of the medical device, the route guidance data are arranged for supporting a user of the medical device in guiding the distal end of the guiding bar near to the entry of the larynx and in passing the medical instrument through the vocal cords into the trachea. This has the advantage that a user of the medical device is technically assisted in conducting a laryngoscopy and/or an intubation. Intubations can be performed with a higher success rate and within shorter time. Operators using the medical device which have a limited degree of experience can be technically supported and educated in performing successful intubations.

The images of the first and/or second camera can be displayed on one or more display units. A display unit can be mounted on the handle of the medical device or on the distal part of the arm of a user. It is also possible to use a display unit mounted on a separate frame. Display units of different size can be used, whereby a display unit adapted to be mounted on the arm of a user can have a size of 7×12 cm. Otherwise, display sizes of 10×15 cm are advantageous. It is advantageous that the display surface of the display unit is less or non-reflective for ambient light.

The picture processing unit can be a computer or part of a computer. On the computer discrete images or sequences of images, like short movies, can be recorded and stored in an electronic documentation system. Also, a direct transmission of the images to a remote place is possible, which supports a distributed support by medical experts. The gathered images can also be used for training purposes, discussions and online-conferences. For this purpose, the medical device can be equipped or coupled to a microphone which allows for direct communication with remotely located other persons. Further, in addition to a microphone an additional camera can be foreseen, e.g. located on or near the display unit, for allowing a visual contact between the user of the medical device and remotely located persons.

According to an advantageous embodiment of the invention, the first camera is arranged and adjusted for capturing an area in front of the distal end of the guiding bar from a position on a side of the guiding bar, e.g. from the left or from the right side, when viewed from above, which means in a direction where the at least partially open portions of the guiding bar in the first bending area are visible. For example, the first camera can be mounted at a side position at the end of the guiding bar. According to an advantageous embodiment of the invention, the capturing direction of the first camera is directed from the one side of the guiding bar to the opposite side of the guiding bar in a diagonal direction, e.g. in an angle of about 30° to the plane which is spanned by the first bending area of the guiding bar.

BRIEF DESCRIPTION OF THE DRAWINGS

The invention is further described by means of examples using several drawings.

The drawings show.

DETAILED DESCRIPTION

Figure 1:
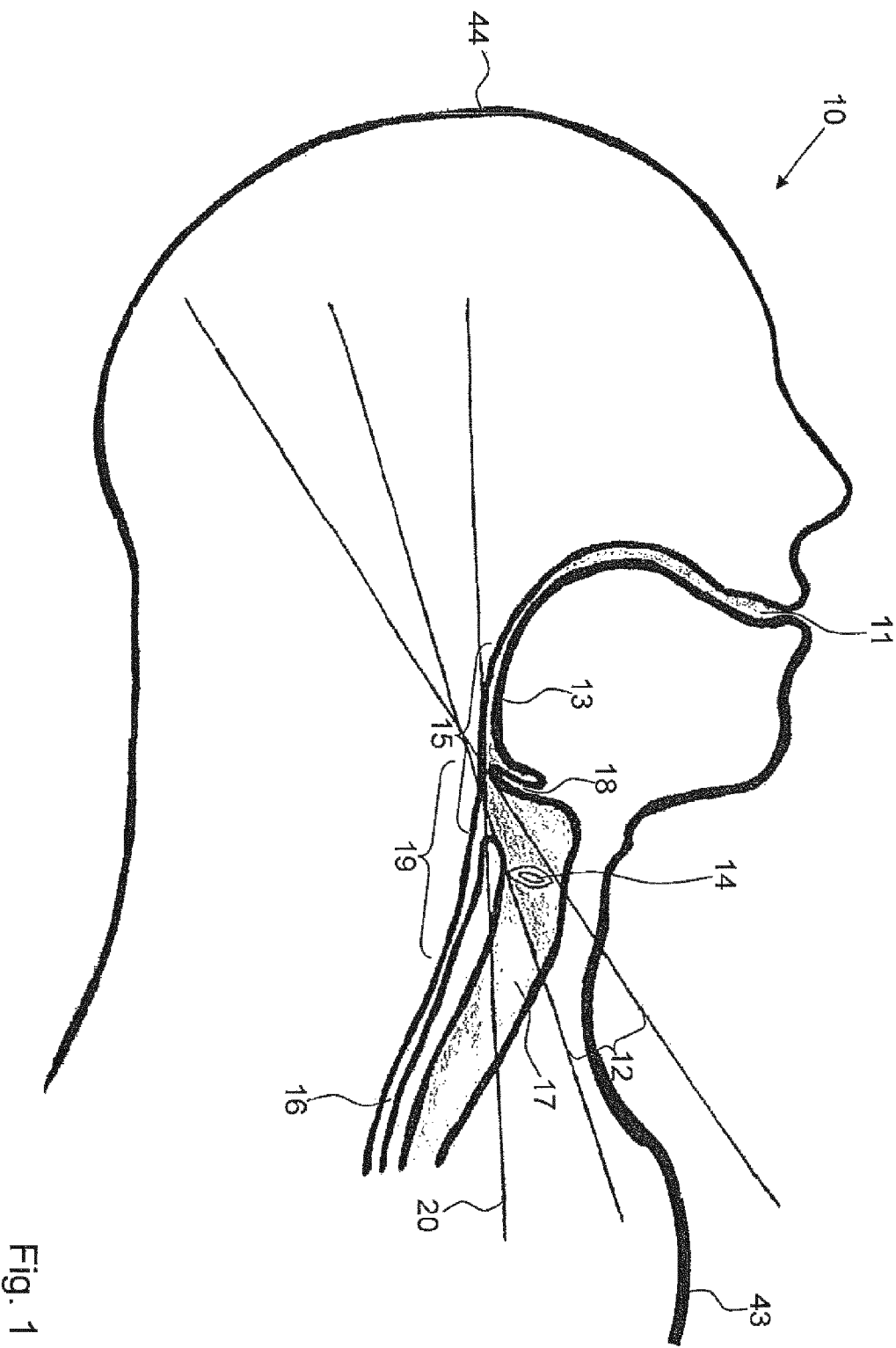
FIG. 1—an upper part of a horizontally lying patient shown as a sectional drawing and FIG. 2—a first embodiment of the medical device in a side view and FIG. 3—a second embodiment of the medical device in a side view and FIG. 4—the second embodiment of the medical device in a front view and FIG. 5—a handle 2 of a medical device and a processing and displaying unit, and FIG. 6—a third embodiment of the medical device in a top view.

In the drawings same numerals are used for same elements.

FIG. 1 shows the upper part of a lying person 10 from the head 44 to the thorax 43. Parts of the airway system of the person 10 are shown in a sectional view. FIG. 1 shows the oral cavity 11, the tongue base 13, the pharynx 15, the larynx 19, the epiglottis 18, the trachea 17, the vocal cords 14 and the esophagus 16. During a laryngoscopy and/or an intubation, a medical device, conventionally a laryngoscope, is inserted through the oral cavity 11 towards the tongue base 13 to enable the direct view to the larynx 19, the entry to the trachea 17. As it can be seen, the airways from the mouth to the trachea 17 are relatively narrow and angled. This makes a laryngoscopy and/or an intubation in some cases very difficult as the tongue base and the epiglottis have to be lifted up not only with conventional laryngoscopy but also with modern video-laryngoscopy to visualize the vocal cords 14.

A line 20 depicts the usual viewing angle of conventional laryngoscopes comprising optical image gathering means. As it can be seen, there is no free view into the entry of the trachea 17 and to the vocal cords 14. With the medical device of the invention, an improved viewing area 12 can be achieved which includes a free view into the entry of the trachea 17 and to the vocal cords 14, which is not covered by the epiglottis 18.

Figure 2:
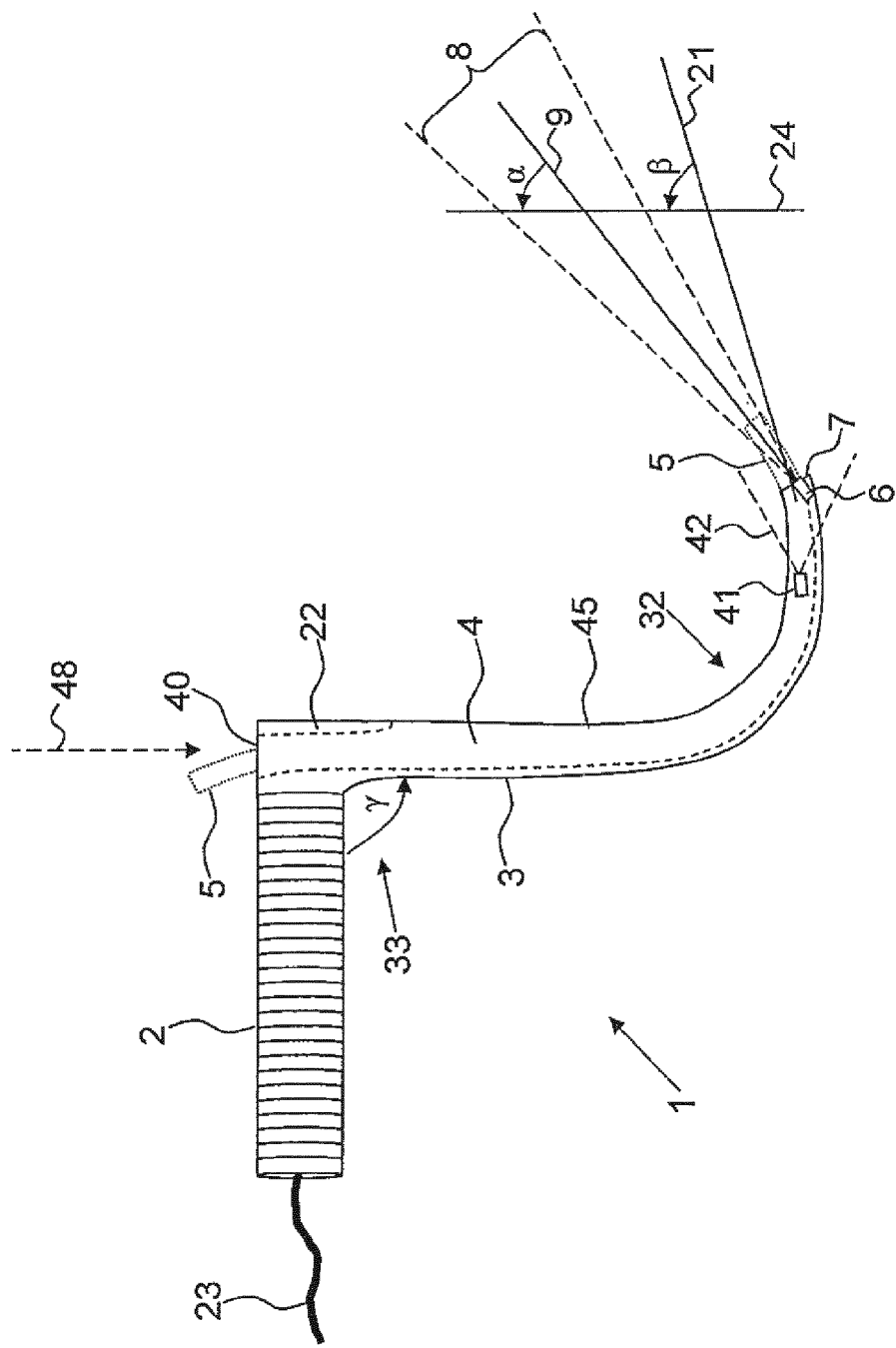

FIG. 2 shows a first embodiment of a medical device 1. The medical device 1 comprises a handle to be hold by an operator with one hand, e.g. the left hand. Rigidly connected to the handle 2 is a guiding bar 3 which can be a rail-like member. The guiding bar 3 comprises a guiding duct 4 adapted for guiding an oral-tracheal tube 5. The guiding duct 4 can be in the form of a channel which means that the guiding bar 3 comprises a backside wall and left and right side walls. The guiding bar 3 can comprise a top wall which is located on the inside of the lower curved portion of the guiding bar 3 and on the opposite side of the handle 2. However, a top wall is not necessary in any case, therefore the guiding bar 3 can be made without a top wall or with only partial sections of a top wall. FIG. 2 shows with broken lines the backside wall of the guiding bar 3 and a partial top wall 22. The profile of the guiding bar 3 can be e.g. U-shaped or rounded.

The guiding bar 3 comprises an entry 40 for the tube 5 which is close to the handle 2. The upper part of the guiding bar 3, close to the entry 40, is arranged with an angle γ of about 90° in relation to the handle 2. The tube 5 is partially shown in dotted lines in the area of the entry 40 and on the distal end 7 of the guiding bar 3 where the tube 5 exits the guiding bar 3.

The guiding bar 3 can include an insertion support in case the guiding bar 3 has no top wall in the area close to the insertion entry 40. The insertion direction of the tube is shown by an arrow 48 in broken lines. In FIG. 2 the insertion support is established by the partial top wall 22. The insertion support can be foreseen on the guiding bar 3 to support and centre the tube 5 when it is inserted into the insertion entry 40. The insertion support can cover the whole width of the guiding duct or only a part of the width, as shown in FIG. 4 through the partial top wall 22. An insertion support covering only a part of the width of the guiding duct 4 allows for an easy removal of the medical device 1 from the patient when the tube 5 is placed in its final destination position without any risk to extract the tube from its position in the trachea.

The guiding bar 3 comprises a first camera 6 close to the distal end 7 of the guiding bar 3. The first camera 6 can be connected via an electrical line. The first camera 6 and the electrical line can be integrated within the guiding bar 3 or attached to the guiding bar 3. The electrical line is guided through the handle 2 and exists from the handle 2 in the form of an external connection cable 23 which can be connected to e.g. a display device.

Instead of connections via electrical lines, a wireless interface can be used for the transfer of data from the first camera 6 or other electrical devices to external devices. For example, a Bluetooth interface can be used. The medical device 1 can be equipped with an integrated electrical power source, like a battery. In this case, electrical lines for the power supply can be avoided. This further improved the practical handling of the medical device 1.

The first camera 6 captures an area 8 in front of the distal end 7 of the guiding bar 3. A central line 9 of the capturing area 8 is shown in FIG. 2. Further, a line 21 shows a hypothetical straight extension line of the guiding bar 3 from its distal end 7. Further, a vertical line 24 is parallel to the insertion direction 48 of the tube 5 into the insertion entry 40. An angle α between the central line 9 and the line 24 resp. the insertion direction 48 is smaller than an angle β between the extension line 21 and the line 24 resp. the insertion direction 48. The angle α can be in the area of 50 to 60°. Further, the tube 5 exists the guiding bar 3 in a direction which has a smaller angle than the angle β. Therefore, the tube 5 is directed into the trachea, which can be viewed and controlled by the first camera 6.

As it can be seen in FIG. 2, the tube 5 exists the guiding bar 3 on the distal end 7 in a direction within the capturing area 8. The exiting direction of the tube 5 can be aligned to the central line 9. For this purpose, the guiding duct 4 can comprise a ramp area on the distal end 7 which supports the tube 5 in exiting the guiding bar 3 in upward direction, so that the tube 5 can be easily inserted into the trachea 17.

In an advantageous embodiment, the first camera 6 is located in the middle or on a side of the guiding bar 3 in a way that the tube 5 appears in the centre of the capturing area 8 when the tube 5 passes the vocal cords 14.

A second camera 41 is located on or within the guiding bar 3 with a certain distance to the distal end 7. The second camera 41 has a capturing area 42 which includes the distal end 7 of the guiding bar 3 and the tube 5 exiting from the guiding bar 3, as well as a surrounding area.

There can be further optical image gathering means arranged on the sides of the guiding bar 3 which supports a view like the human binocular viewing perspective. This allows a three dimensional viewing and an estimation of distances. The images delivered by the cameras and other optical image gathering devices can be fed into an image processing means which calculates distances and considers the calculated distances in generating route guidance data.

Further, the first camera 6 can be protected by a protection roof which is on both sides and above the first camera 6, or in particular, the optical lens of the first camera 6. The guiding roof helps to avoid that the mucosa comes into contact with the optical lens. In this way, the guiding roof helps to maintain a clear and undisturbed vision of the first camera 6. Of course, the protection roof does not cover the capturing area 8.

The medical device 1 comprises a first bending area 32 in the lower section of the guiding bar 3. A second bending area 33 is located in the junction area of the guiding bar 3 and the handle 2.

FIGS. 3 and 4 depict a second embodiment of the medical device 1. As it can be seen in FIG. 3, the medical device 1 has an S-shaped design which is adapted to the shape of the oral airways of a human. The second bending area 33 comprises an angle of more than 90°. Also, the first bending area 32 covers an arc angle of more than 90°, like 110°. Within an arc angle range of at least 80° of the first bending 32 area the guiding bar 3 is designed with a constant bending radius.

It can be seen in FIG. 4 that the first camera 6 is not located centrally within the guiding bar 3, but located in a position offset from the center axis of the guiding bar 3, for example on the left side of the guiding bar 3, when viewed from above on the first bending area 32. It is advantageous to adjust the first camera in a way that the capturing direction of the first camera 6 is diagonal, which means that the first camera captures in a direction away from the side of the guiding bar where the first camera 6 is located.

The guiding bar 3 and the handle 2 of the medical device 1 of FIGS. 3 and 4 comprise an integrated flushing and suction system. The flushing and suction system comprises a suction channel 25 in the form of a tube and a flushing channel 26 also in the form of a tube. The suction channel 25 comprises a suction opening 31 close to the distal end 7 of the guiding bar 3. The flushing channel 26 comprises an emission opening 30 located close to the first camera 6 for emitting flushing medium.

Figure 5:
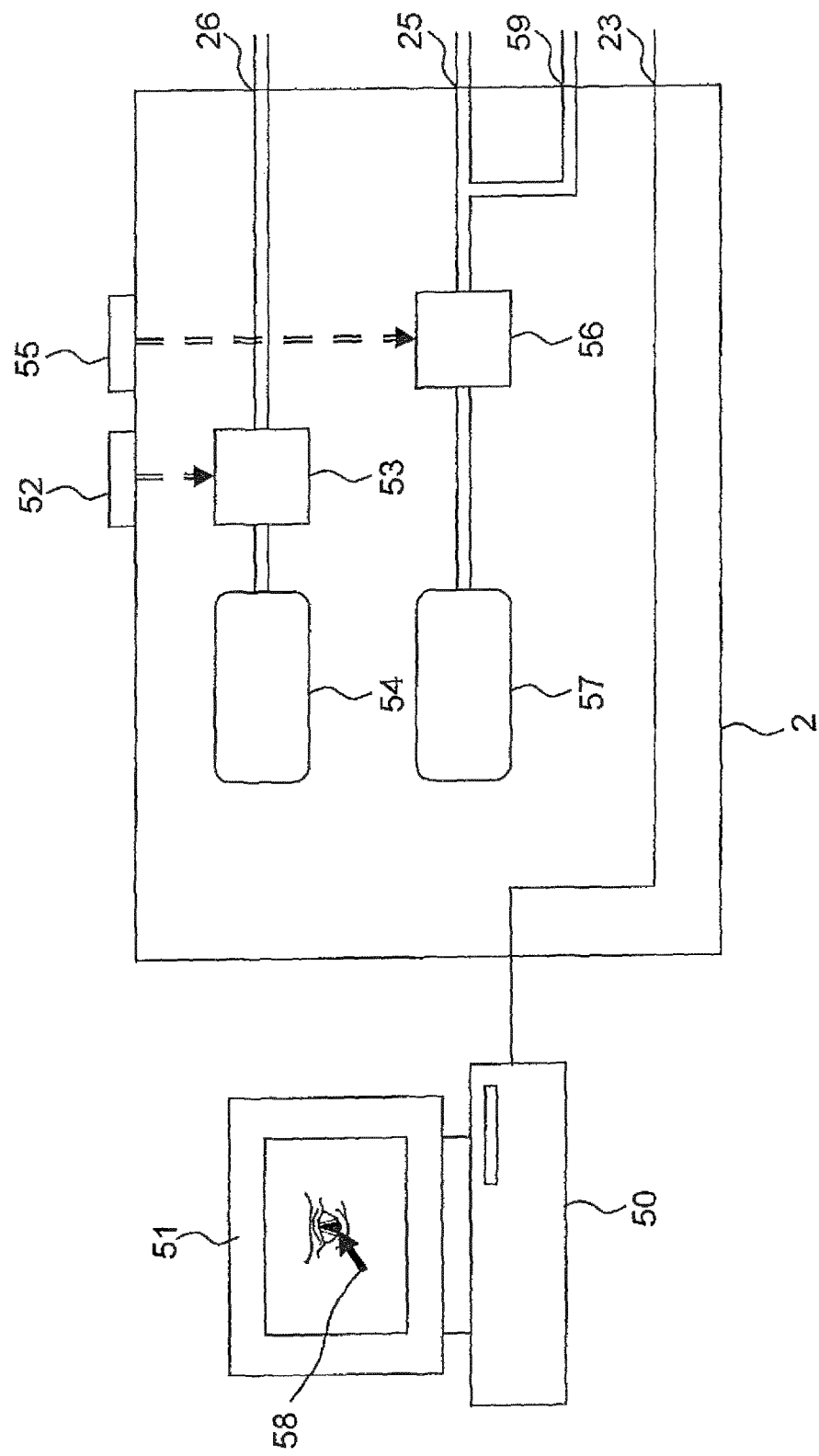

FIG. 5 shows a handle 2 of another embodiment of the medical device 1 with further details. The already mentioned electrical line 23 of the first camera 6 is lead through the handle 2 and connected to an external image processing device 50 and a display device 51. Also, the second camera 41 can be connected in similar manner to the image processing device 50 and the displaying device 51. The image processing device 50 processes the images delivered from the first and/or second camera 6, 41 and displays corresponding images on the display device 51. Further, the image processing device 50 generates route guidance data based on the received and processed images from the first and the second camera. The route guidance data are shown in FIG. 5 in an exemplary manner by an arrow 58. The route guidance data help an user to guide the medical device 1 with its distal end 7 of the guiding bar 3 into the entry of the larynx 19 past the vocal cords 14 into the trachea 17.

The handle 2 further comprises the following elements which are integrated within the handle 2. The handle comprises a liquid container 54 which contains flushing medium. The liquid container 54 is connected to a pumping mechanism 53 which can be manually operated by pressing a button 52 on the handle 2. Through operating the pumping mechanism 53, flushing medium is pumped through the flushing channel 26 to the emission opening 30. Further, the handle comprises a liquid container 57 which is a storage for liquids gathered through the first suction channel 25 and the second suction channel 59. The liquid container 57 is connected to a suction mechanism 56, which can have a similar function like the pumping mechanism 54. The suction mechanism 56 can be operated by pressing a button 55 on the handle 2. Through operating the suction mechanism 56, liquids are sucked from the suction opening 31 through the first suction channel 25 into the liquid container 57, and from a corresponding suction opening through the second suction channel 59 into the liquid container 57.

Figure 6:
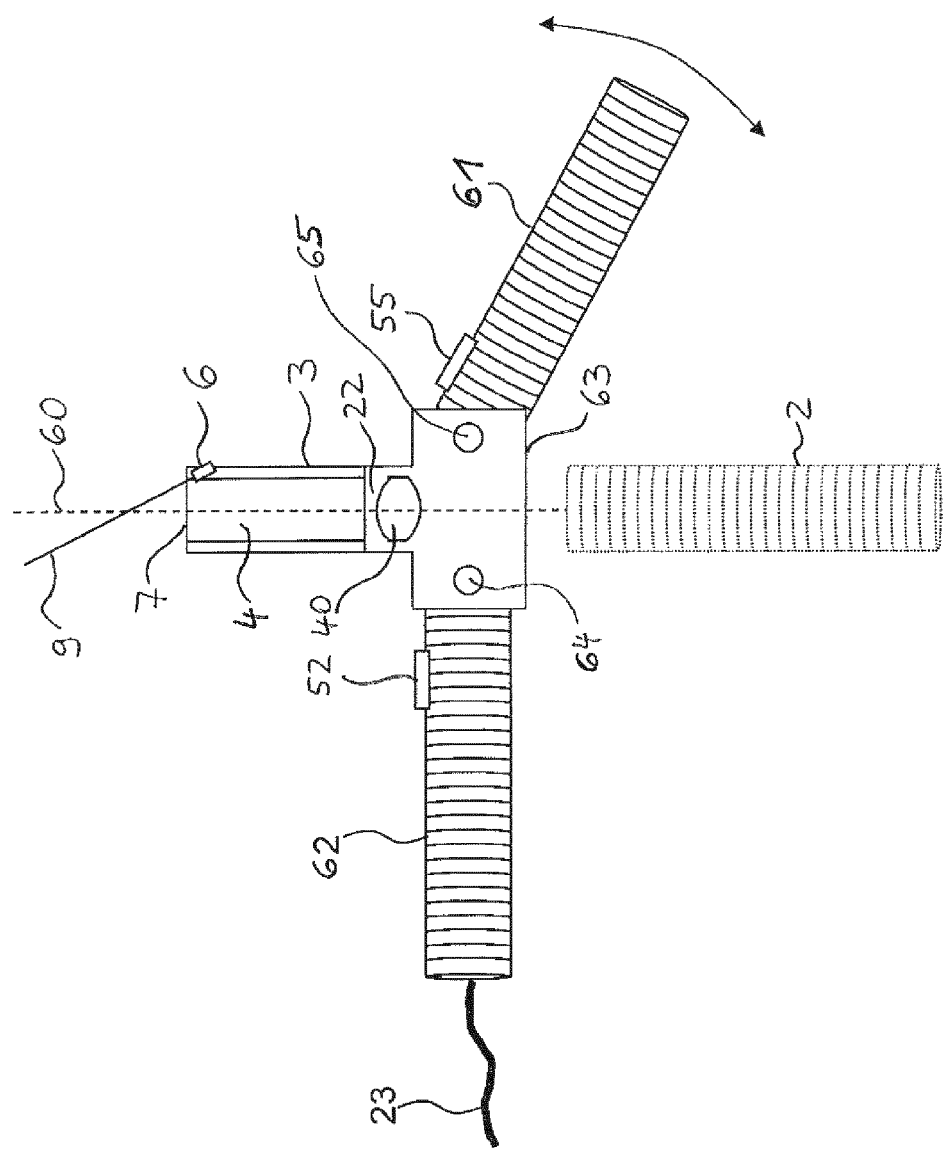

FIG. 6 shows a medical device 1 in a top view, which means in a view in the direction indicated by arrow 48 in FIG. 2. As can be seen in this view, the first camera 6 is located on the right side of the guiding bar 3. Its capturing direction 9 is arranged within an angle to the plane 60 spanned by the curved portion 32 of the guiding bar 3. The capturing direction points to the other side, the left side, of the guiding bar 3.

FIG. 6 shows an embodiment of the medical device which has a first section 62 and a second section 61 of a handle. The two sections 61, 62 of the handle are located symmetrically on both sides of the guiding bar 3. The sections 61, 62 of the handle are connected to a central block 63 of the medical device which carries the guiding bar. The sections 61, 62 are connected to the central block 63 through articulated joints 64, 65. The articulated joints allow for different angular positions of the sections 61, 62 relative to the guiding bar 3, as indicated in FIG. 6 for the second section 61 of the handle by the two-sided arrow.

It is possible to integrate e.g. the button 52 into the first section 62 and the button 55 into the second section 61 of the handle.

FIG. 6 shows only for the purpose of explanation the theoretical position of the handle 2 of the device according to FIG. 2, in case the device of FIG. 2 is viewed from the top.

The invention claimed is:

1. A medical device for conducting a medical examination and/or intervention within a human or animal body, the medical device comprising
 a handle;
 a curved guiding bar connected to the handle, the guiding bar comprising
  a guiding duct configured for guiding a medical instrument from an area of the handle to a distal end of the guiding bar which is a first distance from the handle,
  a curved bending area which is a second distance from the handle,
  wherein the guiding duct is configured as a channel with a backside wall, a left side wall, and a right side wall, wherein the channel has at least one or more partial sections without a top wall such that the curved guiding bar is at least partially open on an inner side of the curved bending area, wherein a top and the inner side of the curved bending area face an anterior direction in a state of use; and
 a first camera at the distalmost end of the guiding bar which is integrated within the guiding bar or attached to the guiding bar, whereby the first camera is arranged and adjusted for capturing an area in front of the distal end of the guiding bar,
 wherein the medical device is sized and configured for conducting a medical examination and/or intervention within a human or animal body without lifting an epiglottis or a tongue base of the human or animal body, wherein the medical device is without a lifter for lifting the epiglottis or the tongue base.

2. The medical device according to claim 1, wherein a first angle between an optical axis of the first camera and an insertion direction of the medical instrument into a proximal end of the guiding duct is smaller than a second angle between a hypothetical straight extension line of the guiding bar from its distal end and the insertion direction of the medical instrument into the proximal end of the guiding duct.

3. The medical device according to claim 1, wherein the guiding bar does not extend into the capturing area of the first camera.

4. The medical device according to claim 1, wherein the guiding duct extends over an entire length of the guiding bar and is arranged for providing a supporting face for the medical instrument within the guiding duct so that the medical instrument lies against the guiding duct.

5. The medical device according to claim 1, further comprising a second camera which is integrated within the guiding bar or attached to the guiding bar between the handle and the distal end of the guiding bar, wherein the second camera is closer to the handle than the first camera, and wherein the second camera is arranged and adjusted for capturing the distal end of the guiding bar and a surrounding area.

6. The medical device according to claim 1, wherein the handle shows away from the thorax of a patient if the medical device is introduced into the patient in the course of conducting a laryngoscopy and/or an intubation.

7. The medical device according to claim 6, wherein the handle shows in the direction of the head of the patient.

8. The medical device according to claim 1, wherein the curved bending area bends at least 90°.

9. The medical device according to claim 8, wherein the curved bending area comprises the same bending radius over an arc angle of at least 80°.

10. The medical device according to claim 8, wherein the at least one or more partial sections of the guiding duct without a top wall are located in the curved bending area.

11. The medical device according to claim 8, further comprising a second bending area of at least 90° in the junction area of the guiding bar and the handle.

12. The medical device according to claim 1, wherein the handle and the guiding bar together have an S-shape when viewed from the side.

13. The medical device according to claim 5, further comprising a flushing channel or a flushing duct for insertion of a flushing conduct, the flushing channel or the flushing duct being integrated within the guiding bar or attached to the guiding bar, wherein the flushing channel or the flushing conduct has at least one emission opening for emitting a flushing medium, wherein the at least one emission opening is located at the distal end of the guiding bar, wherein the at least one emission opening is adjusted in a way that emitted flushing medium is directed to the first and/or second camera.

14. The medical device according to claim 1, wherein the medical device further comprises a first suction channel or a first suction duct for inserting a first suction conduct, the first suction channel or the first suction duct being integrated within the guiding bar or attached to the guiding bar, wherein the first suction channel or the first suction conduct comprises a first suction opening which is located at the distal end of the guiding bar.

15. The medical device according to claim 14, wherein the medical device comprises a second suction channel or a second suction duct for inserting a second suction conduct, the second suction channel or the second suction duct being integrated within the guiding bar or attached to the guiding bar, wherein the second suction channel or the second suction conduct comprises a second suction opening which is located at the distal end of the guiding bar, wherein the second suction opening is adjusted in a way that flushing medium is extractable by suction.

16. The medical device according to claim 1, wherein one or more of the following elements are included within the handle:
a) a liquid container in the form of a reservoir for flushing medium,
b) a pumping mechanism for delivery of flushing medium, the pumping mechanism being connected to the reservoir for flushing medium,
c) a liquid container in the form of a storage for liquids gathered through a suction channel or a suction conduct through suction, and
d) a suction mechanism for removal of liquids, which is connected to the liquid container.

17. The medical device according to claim 5, further comprising a picture processing unit coupled to one or more of the first and second camera, the picture processing unit being configured for processing of pictures delivered by the first and/or second camera by means of pattern recognition and for identifying the actual position of the distal end of the medical device during a laryngoscopy and/or intubation within the patient, wherein the picture processing unit is configured for generating route guidance data based on the identified actual position of the distal end of the medical device, wherein the route guidance data are configured for supporting a user of the medical device in guiding the distal end of the guiding bar near to the entry of the larynx and in guiding a medical instrument to pass the vocal cords into the trachea.

18. The medical device according to claim 1, wherein a longitudinal axis of the handle is approximately perpendicular to a plane which is spanned by the curved bending area of the medical device.

19. The medical device according to claim 1, wherein the handle of the medical device comprises a first section and a second section, with the guiding bar being fixed to the medical device between the first and second sections of the handle.

20. The medical device according to claim 19, wherein the first section of the handle comprises control elements for controlling a flushing mechanism of the medical device and the second section comprises control elements for controlling a suction mechanism of the medical device.

21. The medical device according to claim 1, wherein the first camera is arranged and adjusted for capturing an area in front of the distal end of the guiding bar from a position on a side of the guiding bar.

22. The medical device according to claim 21, wherein the capturing direction of the first camera is directed from one side of the guiding bar to the an opposite side of the guiding bar in a diagonal direction.

23. The medical device according to claim 1, wherein the guiding bar is connected to the handle via an articulated joint which allows positioning of the handle in different angles relative to the guiding bar.

24. The medical device according to claim 23, wherein the articulated joint comprises a notch mechanism which allows for fixation of the angular position of the handle relative to the guiding bar through a number of predefined notching positions.

* * * * *